(12) United States Patent
Chen et al.

(10) Patent No.: US 7,764,997 B2
(45) Date of Patent: Jul. 27, 2010

(54) METHOD AND APPARATUS FOR USING ATRIAL DISCRIMINATION ALGORITHMS TO DETERMINE OPTIMAL PACING THERAPY AND THERAPY TIMING

(75) Inventors: Victor T. Chen, Minnetrista, MN (US); David S. Wood, Temecula, CA (US); Milton M. Morris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 607 days.

(21) Appl. No.: 11/266,955

(22) Filed: Nov. 4, 2005

(65) Prior Publication Data

US 2006/0058849 A1 Mar. 16, 2006

Related U.S. Application Data

(62) Division of application No. 09/712,600, filed on Nov. 14, 2000, now Pat. No. 6,978,177.

(51) Int. Cl.
*A61N 1/00* (2006.01)
(52) U.S. Cl. .......................................... 607/4; 607/14
(58) Field of Classification Search ................ 607/4–28
See application file for complete search history.

(56) References Cited

U.S. PATENT DOCUMENTS

| | | | |
|---|---|---|---|
| 4,336,810 A | 6/1982 | Anderson et al. |
| 4,531,527 A | 7/1985 | Reinhold, Jr. et al. |
| 4,721,114 A | 1/1988 | DuFault et al. |
| 4,869,252 A | 9/1989 | Gilli |
| 4,924,875 A | 5/1990 | Chamoun |
| 4,998,974 A | 3/1991 | Aker |
| 5,000,189 A | 3/1991 | Throne et al. |
| 5,107,850 A | 4/1992 | Olive |
| 5,139,028 A | 8/1992 | Steinhaus et al. |

(Continued)

FOREIGN PATENT DOCUMENTS

EP  0 469 817 A2  2/1992

(Continued)

OTHER PUBLICATIONS

Ellenbogen, Kenneth A., "Cardiac Pacing", Cambridge, Mass., USA : *Blackwell Science*, 2nd ed., (1996),311-312 & 435-437.

(Continued)

*Primary Examiner*—Scott M Getzow
(74) *Attorney, Agent, or Firm*—Schwegman, Lundberg, Woessner, P.A.

(57) ABSTRACT

A system and method which employs atrial discrimination algorithms to distinguish between different atrial arrhythmias occurring in a patient for selecting an optimal pacing therapy corresponding to the type of arrhythmia identified. In response to the detection of an atrial rate above the atrial tracking rate, discrimination criteria are applied to a detected atrial activity signal to distinguish between different types of supraventricular tachycardia, such as fast atrial flutter and other atrial flutter at a relatively slower rate, which may be occurring in the patient. The pacer is controlled to provide pacing therapy to a heart in a manner corresponding to the type of supraventricular tachycardia identified. The output of an atrial discrimination algorithm may be tracked and the trend thereof used to improve therapy timing. Various embodiments are disclosed herein.

26 Claims, 3 Drawing Sheets

U.S. PATENT DOCUMENTS

| | | | |
|---|---|---|---|
| 5,161,527 A * | 11/1992 | Nappholz et al. | 607/14 |
| 5,184,615 A | 2/1993 | Nappholz et al. | |
| 5,193,535 A | 3/1993 | Bardy et al. | |
| 5,193,550 A | 3/1993 | Duffin | |
| 5,205,283 A * | 4/1993 | Olson | 607/4 |
| 5,240,009 A | 8/1993 | Williams | |
| 5,271,411 A | 12/1993 | Ripley et al. | |
| 5,273,049 A | 12/1993 | Steinhaus et al. | |
| 5,282,836 A | 2/1994 | Kreyenhagen et al. | |
| 5,292,348 A | 3/1994 | Saumarez et al. | |
| 5,311,874 A | 5/1994 | Baumann et al. | |
| 5,312,445 A | 5/1994 | Nappholz et al. | |
| 5,313,953 A | 5/1994 | Yomtov et al. | |
| 5,342,402 A | 8/1994 | Olson et al. | |
| 5,356,425 A | 10/1994 | Bardy et al. | |
| 5,366,487 A | 11/1994 | Adams et al. | |
| 5,383,910 A | 1/1995 | den Dulk | |
| 5,388,578 A | 2/1995 | Yomtov et al. | |
| 5,411,031 A | 5/1995 | Yomtov | |
| 5,458,623 A | 10/1995 | Lu et al. | |
| 5,462,060 A | 10/1995 | Jacobson et al. | |
| 5,520,191 A | 5/1996 | Karlsson et al. | |
| 5,545,186 A | 8/1996 | Olson et al. | |
| 5,549,641 A | 8/1996 | Ayers et al. | |
| 5,560,369 A | 10/1996 | McClure et al. | |
| 5,605,159 A | 2/1997 | Smith et al. | |
| 5,682,900 A | 11/1997 | Arand et al. | |
| 5,683,425 A | 11/1997 | Hauptmann | |
| 5,713,367 A | 2/1998 | Arnold et al. | |
| 5,725,561 A | 3/1998 | Stroebel et al. | |
| 5,730,141 A | 3/1998 | Fain et al. | |
| 5,755,736 A | 5/1998 | Gillberg et al. | |
| 5,755,737 A | 5/1998 | Prieve et al. | |
| 5,759,196 A * | 6/1998 | Hess et al. | 607/14 |
| 5,779,645 A | 7/1998 | Olson et al. | |
| 5,788,717 A | 8/1998 | Mann et al. | |
| 5,792,065 A | 8/1998 | Xue et al. | |
| 5,797,849 A | 8/1998 | Vesely et al. | |
| 5,814,081 A | 9/1998 | Ayers et al. | |
| 5,819,007 A | 10/1998 | Elghazzawi | |
| 5,819,741 A | 10/1998 | Karlsson et al. | |
| 5,836,975 A | 11/1998 | DeGroot | |
| 5,846,263 A | 12/1998 | Peterson et al. | |
| 5,855,593 A | 1/1999 | Olson et al. | |
| 5,873,897 A | 2/1999 | Armstrong et al. | |
| 5,893,882 A | 4/1999 | Peterson et al. | |
| 5,928,271 A | 7/1999 | Hess et al. | |
| 5,931,857 A | 8/1999 | Prieve et al. | |
| 5,968,079 A | 10/1999 | Warman et al. | |
| 5,987,356 A | 11/1999 | DeGroot | |
| 5,991,656 A | 11/1999 | Olson et al. | |
| 5,991,657 A | 11/1999 | Kim | |
| 6,052,620 A | 4/2000 | Gillberg et al. | |
| 6,076,014 A | 6/2000 | Alt | |
| 6,096,061 A | 8/2000 | Alt | |
| 6,181,364 B1 | 1/2001 | Ford | |
| 6,212,428 B1 | 4/2001 | Hsu et al. | |
| 6,223,078 B1 | 4/2001 | Marcovecchio | |
| 6,266,554 B1 | 7/2001 | Hsu et al. | |
| 6,275,732 B1 | 8/2001 | Hsu et al. | |
| 6,285,907 B1 | 9/2001 | Kramer et al. | |
| 6,308,095 B1 | 10/2001 | Hsu et al. | |
| 6,312,388 B1 | 11/2001 | Marcovecchio et al. | |
| 6,314,321 B1 | 11/2001 | Morris | |
| 6,351,669 B1 | 2/2002 | Hartley et al. | |
| 6,353,759 B1 | 3/2002 | Hartley et al. | |
| 6,411,848 B2 | 6/2002 | Kramer et al. | |
| 6,430,435 B1 | 8/2002 | Hsu et al. | |
| 6,430,438 B1 | 8/2002 | Chen et al. | |
| 6,438,410 B2 | 8/2002 | Hsu et al. | |
| 6,442,425 B1 | 8/2002 | Alt | |
| 6,449,503 B1 | 9/2002 | Hsu | |
| 6,484,055 B1 | 11/2002 | Marcovecchio | |
| 6,501,988 B2 | 12/2002 | Kramer et al. | |
| 6,512,951 B1 | 1/2003 | Marcovecchio et al. | |
| 6,687,540 B2 | 2/2004 | Marcovecchio | |
| 6,978,177 B1 | 12/2005 | Chen et al. | |
| 7,039,463 B2 | 5/2006 | Marcovecchio | |
| 2004/0116972 A1 | 6/2004 | Marcovecchio | |
| 2006/0122527 A1 | 6/2006 | Marcovecchio | |

FOREIGN PATENT DOCUMENTS

| | | |
|---|---|---|
| EP | 0 506 230 | 9/1992 |
| EP | 0554208 | 8/1993 |
| EP | 0711531 | 5/1996 |
| EP | 0776631 | 11/1996 |
| EP | 0848965 | 6/1998 |
| WO | WO-93/02746 | 2/1993 |
| WO | WO-97/39681 | 4/1996 |

OTHER PUBLICATIONS

Jung, J., et al., "Discrimination of Sinus Rhythm, Atrial Flutter, and Atrial Fibrillation Using Bipolar Endocardial Signals", *Journal of Cardiovascular Electrophysiology*, 9 (7), (Jul. 1998),pp. 689-695.

Krig, D. B., et al., "Method and Apparatus for Treating Irregular Ventricular Contractions Such as During Atrial Arrhythmia", U.S. Appl. No. 09/316,515, filed May 21, 1999, 57 pages.

Morris, Milton M., "Detection of Atrial Arrhythmia for Cardiac Rhythm Management by Implantable Devices", *Journal of Electrocardiology*, vol. 33, (2000),133-139.

Wittkampf, F.H.M., et al., "Rate Stabilization by Right Ventricular Patching in Patients with Atrial Fibrillation", *Pace, 9*, (Nov.-Dec. 1986),1147-1153.

* cited by examiner

METHOD AND APPARATUS FOR USING ATRIAL DISCRIMINATION ALGORITHMS TO DETERMINE OPTIMAL PACING THERAPY AND THERAPY TIMING

CROSS-REFERENCE TO RELATED APPLICATION(S)

This application is a division of U.S. patent application Ser. No. 09/712,600, filed on Nov. 14, 2000, now issued as U.S. Pat. No. 6,978,177, the specification of which is incorporated herein by reference.

FIELD OF THE INVENTION

The present invention pertains generally to medical devices and more particularly to medical devices for monitoring activity of the heart and providing therapy thereto including implantable bradycardia pacemakers and the like.

BACKGROUND OF THE INVENTION

Various types of medical devices are employed to monitor electrical or other activity of the heart and to provide therapy to the heart in response to the detection of irregular cardiac rhythms. Such devices may be implantable beneath the skin of a patient, i.e., in the patient's chest. Such implantable devices include a hermetically sealed canister containing electronic circuitry for implementing the functions of the device, one or more electrodes implanted in one or more of the ventricles or atria of the heart, or in close proximity thereto, and leads for connecting the electrodes to the circuitry within the device canister. The device circuitry includes circuitry for detecting electrical signals produced by the heart, which signals are picked up at the electrodes, along with circuitry, typically implemented in a microprocessor, for analyzing the thus detected cardiac signals. The device may also include circuitry for providing therapy in the form of electrical signals applied to the heart. Such signals are provided to the heart, via the leads and electrodes mounted in the heart, in response to the detection of an irregular cardiac rhythm by the analysis circuitry based on the detected cardiac activity signals. The implantable device may also include a transmitter/receiver, for transmitting cardiac activity and other information to an external device for, e.g., storage and/or further analysis, and for receiving information, such as programming instructions, from the external device via, for example, an RF link.

An example of such an implantable cardiac device is a bradycardia pacemaker. A bradycardia pacemaker provides relatively low level electrical pulses to the heart to stimulate heart activity when the natural cardiac rate provided by the heart is too low. A dual chamber bradycardia pacemaker includes electrodes positioned in both the atria and ventricles of the heart for detecting naturally occurring atrial and ventricular activations and for providing pacing pulses to the atria and/or ventricles as needed. Such a device monitors the time between sensed and paced atrial and ventricular activations and provides pacing pulses as needed to maintain an adequate heart rate. For example, such a device will note the occurrence of a sensed or paced atrial or ventricular event and, if a subsequent naturally occurring atrial and/or ventricular event is not sensed within a certain time (escape interval) following the fist sensed or paced event, a pacing pulse will be applied to the atria and/or ventricles to maintain a desired heart rate.

Although the primary purpose of a bradycardia pacemaker is to provide therapy for heart rates which are too slow, such pacemakers are also typically programmed to deal with naturally occurring atrial and ventricular rates which are too rapid. For example, such a device may detect a too-rapid ventricular rate (ventricular tachycardia). Antitachycardia pacing may be provided to the ventricles to attempt to terminate the ventricular tachycardia. Antitachycardia pacing typically involves a train of pacing pulses applied to the ventricles at a rate slightly higher than the rate of the tachycardia.

In many cases, a bradycardia pacemaker will be programmed to pace the ventricles of the heart so as to track the naturally occurring atrial rate. This is effective in many patients wherein the natural pacemaker which initiates a cardiac cycle in the atria performs normally most of the time. In such a case, the naturally occurring atrial rate is representative of the metabolic demand of the patient (e.g., the atrial rate will increase during exercise or other activity, and decrease during rest periods). Thus, pacing the ventricles to track the atrial rate in such a case ensures an adequate pacing rate for the patient's metabolic demand. However, if the naturally occurring atrial rate becomes too rapid, i.e., a pathologic atrial rhythm (atrial tachycardia) occurs, too rapid ventricular pacing may result if the pacemaker continues to track the atrial rate. Typical bradycardia pacemakers are programmed to deal with such supraventricular rhythm disturbances by automatically switching from an atrial tracking mode of operation (e.g., DDD or DDDR mode) to a mode of operation which does not track the atrial rate (e.g., VVI or VVIR mode) when the detected atrial rate exceeds a maximum atrial tracking rate or another pathological atrial rhythm is sensed by the pacemaker which may otherwise result in too rapid ventricular pacing.

Another type of implantable cardiac device is a defibrillator. A defibrillator detects for very rapid irregular rhythms (fibrillation) in the atria or ventricles. In response to the detection of fibrillation, the defibrillator provides a relatively high energy electrical defibrillation shock to the chambers of the heart which are in fibrillation to attempt to defibrillate the heart to return to a normal sinus rhythm. Rapid detection and defibrillation of ventricular fibrillation is critical. During ventricular fibrillation no blood is circulated by the heart, therefore, rapid defibrillation is required to prevent death. Atrial fibrillation is typically treated by a relatively high energy level shock provided to the atria in synchronism with a ventricular activation (atrial cardioversion). The atrial shock is provided in synchronism with a ventricular depolarization to prevent the attempted atrial cardioversion from inducing a more serious ventricular arrhythmia.

Many modern implantable cardiac devices combine the features of a cardiac pacemaker with those of a cardiac defibrillator. Such devices provide bradycardia pacing in a normal manner, along with monitoring of the ventricles and/or atria to detect for occurrences of ventricular or atrial fibrillation. If ventricular or atrial fibrillation is detected, defibrillating or cardioverting electrical energy is applied to the ventricles or atria in a conventional manner in an attempt to restore a more stable cardiac rhythm. Such devices may incorporate algorithms for distinguishing between, e.g., different rates of ventricular tachycardia, which may be pacing terminable, e.g., via antitachycardia pacing, and ventricular fibrillation, which is not pacing terminable, i.e., requires defibrillation. An example of such an algorithm is described, for example, in U.S. Pat. No. 5,342,402 to Olson, et al. U.S. Pat. No. 6,314,321, filed Jun. 30, 1999, by Milton M. Morris, and entitled Therapy-Selection Methods for Implantable Heart Monitors, which application is assigned to the assignee of the present application, describes an algorithm for distinguishing between pacing terminable and non-pacing terminable atrial and ventricular arrythmias. An implantable cardiac device may also distinguish between different degrees of atrial fibrillation, e. g., between atrial fibrillation of high disorganization and atrial fibrillation of intermediate organization, to provide different levels of atrial defibrillation therapy depending upon the degree of disorganization. The application of such a function in an atrial defibrillator is described in U.S. Pat. No. 5,549,641 to Ayers, et al.

A limitation of current bradycardia pacemakers and similar implantable cardiac devices is the response of such devices to detected supraventricular tachycardias, such as atrial flutter. Supraventricular tachycardias are rapid heart rates due to a pacemaker anywhere above the ventricular level, i.e., the sinus node, the atria, or the atria ventricular junction. Atrial flutter, in particular, is a rapid regular atrial contraction. As discussed above, a typical bradycardia pacemaker will respond to a supraventricular tachycardia by mode switching such that ventricular pacing does not track the atrial rate. Nevertheless, a rapid supraventricular arrythmia may induce a ventricular arrhythmia as well. What is desired, therefore, is an implantable pacemaker or other cardiac device which controls a pacemaker to provide an appropriate pacing therapy in response to the detection of a supraventricular tachycardia. In particular, what is desired is an implantable cardiac pacemaker or other device which employs discrimination algorithms to distinguish between different rapid regular atrial arrhythmias (e.g., fast atrial flutter and other atrial flutter) and which provides an appropriate pacing therapy, in either the atria or ventricles, corresponding to the type of arrhythmia identified.

SUMMARY OF THE INVENTION

The present invention provides a system and method which employs atrial discrimination algorithms to distinguish between different atrial arrhythmias occurring in a patient for selecting an optimal pacing therapy corresponding to the type of arrhythmia identified. The present invention may be implemented, for example, in an otherwise conventional bradycardia pacemaker or other implantable cardiac device. In a bradycardia pacemaker, for example, in response to the detection of an atrial rate above the atrial tracking rate, discrimination criteria are applied to a detected atrial activity signal to distinguish between different types of supraventricular tachycardia which may be occurring. For example, the discrimination criteria may be included in a discrimination algorithm for distinguishing between the occurrence of a high rate atrial flutter and a relatively lower rate supraventricular tachycardia. Pacer circuitry may then be controlled to provide optimal pacing in response to the type of atrial arrhythmia detected.

The present invention may be implemented in an implantable cardiac device which includes signal detection circuitry connected via leads to electrodes positioned in the atria and/or ventricles of the heart. Pacer circuitry paces the heart using relatively low level electrical signals provided on the leads to the electrodes in a conventional manner to provide a bradycardia pacemaker function. A system processor monitors the output provided by the signal detection circuitry to detect the occurrence of a rapid atrial rate, e.g., an atrial rate above the maximum atrial tracking rate of the pacer. If an atrial rate above the maximum atrial tracking rate is detected by the processor, the processor analyzes a cardiac activity signal provided by the signal detection circuitry using an atrial discrimination algorithm for distinguishing between different types of supraventricular tachycardias/atrial flutter which may be occurring. The implantable device may also include a defibrillator/cardioverter for providing defibrillation/cardioversion of the ventricles and/or atria in response to the detection of ventricular or atrial fibrillation which is not pacing terminable. The implantable device is preferably also provided with a receiver/transmitter coupled to the processor to allow the processor to transmit cardiac activity or other data to an external device for storage and/or further analysis and to receive data, such as programming instructions, from the external device.

The atrial discrimination algorithm employed by the processor includes discrimination criteria for distinguishing between different types of supraventricular tachycardia. In particular, the atrial discrimination algorithm preferably distinguishes between relatively rapid regular atrial contractions which correspond to atrial flutter and relatively lower rate regular atrial contractions which correspond to another type of supraventricular tachycardia (e.g., other atrial flutter). The atrial discrimination algorithm may incorporate rate-based or other discrimination criteria for distinguishing between different types of supraventricular tachycardia/atrial flutter based on the timing of detected atrial depolarizations. Alternatively, or additionally, the atrial discrimination algorithm may incorporate morphology-based discrimination criteria for distinguishing between different types of supraventricular tachycardia/atrial flutter based on morphology characteristics of an atrial activity (e.g., electrogram) signal. In either case, the atrial discrimination algorithm provides an indication of the type of supraventricular tachycardia/atrial flutter which is occurring.

In accordance with the present invention, an implantable cardiac device controls the pacing of the heart in an optimal manner corresponding to the type of supraventricular tachycardia identified by the atrial discrimination algorithm. For example, in response to the detection of a relatively lower rate supraventricular tachycardia (other atrial flutter) the device preferable provides atrial antitachycardia pacing in the form of a rapid train of pacing pulses to the atria. In response to the identification of a rapid atrial flutter (fast atrial flutter), which is too rapid to respond to atrial antitachycardia pacing, the device may be controlled to provide another type of pacing therapy, in particular, ventricular pacing such as ventricular rate regulation or Rate Smoothing.

The atrial discrimination algorithm may also be employed to optimize the timing of therapy delivery. By employing the algorithm output to track and trend the behavior of a supraventricular tachycardia over time, the optimum timing of pacing therapy delivery may be determined.

A method or device for distinguishing between different types of supraventricular tachycardia/atrial flutter in a bradycardia pacing or other device in accordance with the present invention also allows for comprehensive diagnostics for atrial arrhythmias of patients in which the device is implanted. For example, the atrial discrimination algorithm may be employed to trend/track the behavior of an atrial arrhythmia over time.

Further objects, features, and advantages of the invention will be apparent from the following detailed description taken in conjunction with the accompanying drawings.

DETAILED DESCRIPTION OF THE INVENTION

Figure 1:
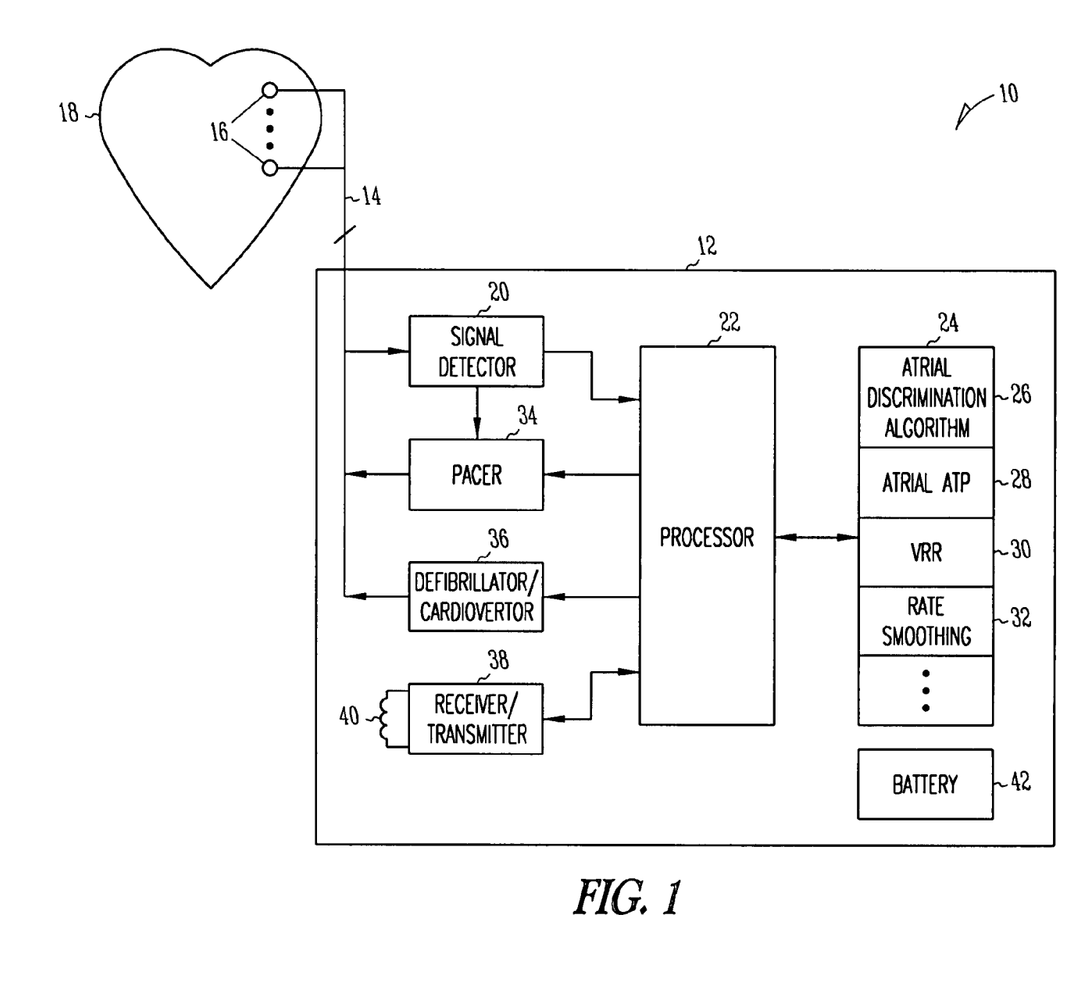
FIG. 1 is a schematic diagram of an exemplary implantable cardiac device incorporating a system and method employing atrial discrimination algorithms for determining optimal pacing therapy and therapy timing in accordance with the present invention.

An exemplary implantable cardiac device 10 incorporating a system and method for using atrial discrimination algorithms to determine optimal pacing therapy in accordance with the present invention is illustrated in, and will be described in detail with reference to, FIG. 1. The implantable cardiac device 10 includes a hermetically sealed canister 12 which encloses circuitry for detecting and analyzing cardiac arrhythmias and for providing therapy therefore, as will be discussed in more detail below. The circuitry within the canister 12 is connected via one or more leads 14 to one or more electrodes 16 which are implanted in or near the chambers of a patient's heart 18. Depending upon the specific application and functionality of the implantable cardiac device 10, electrodes 16 may be positioned in or near the ventricles, atria or, preferably, both the atria and ventricles of the heart 18. The electrodes 16 pick up electrical signals produced in the chambers of the heart 18 and provide electrical contact for electrical pulses or shocks which are delivered to the chambers of the heart 18 to pace or defibrillate/cardiovert the heart 18. In a dual chamber bradycardia pacemaker, for example, electrodes 16 are positioned in or near both the atria and ventricles of the heart 18 to detect atrial and ventricular activity of the heart 18 and to provide pacing pulses to the atria and ventricles. A plurality of leads 14 may be required to connect the electrodes 16 positioned in or near the heart 18 to the circuitry within the device canister 12. As is known in the art, multiple electrodes 16 may be coupled to the circuitry within the canister 12 via a single one of the leads 14. The canister 12, leads 14, and electrodes 16 are preferably designed such that the entire device 10 is implantable beneath the skin of a patient.

The leads 14 connect the electrodes 16 positioned within or near the heart 18 to signal detection circuitry 20 within the implantable device canister 12. The signal detection circuitry 20 may be implemented in a conventional manner to provide atrial and/or ventricular activity signals based on the cardiac signals picked up at the electrodes 16. Conventional signal detection circuitry 20 may include signal amplifiers and filters, and may include, in addition, circuitry for detecting atrial and ventricular depolarizations and providing atrial and ventricular depolarization detection indication signals in response thereto along with circuitry for obtaining electrogram signals and providing digitized electrograms from the cardiac signals detected at the electrodes 16.

The signals provided by the signal detection circuitry 20 are provided to a system processor 22. The system processor 22 may be implemented, for example, as one or more conventional microprocessors with associated memory 24. Memory 24 may be an integral part of or separated from, but coupled to, the processor 22. Memory 24 is employed in a conventional manner to store data, such as cardiac activity data, for analysis by the processor 22, as well as to store the programming instructions which control the functions performed by the processor 22. For example, programming instructions for implementing an atrial discrimination algorithm 26 by the processor 22, and for operating the processor 22 to control the cardiac device 12 to provide various different pacing therapies, such as atrial antitachycardia pacing 28, ventricular rate regulation 30, and Rate Smoothing 30, etc. may be stored in memory 24. These functions will be described in more detail below. Of course, other general and conventional programming instructions for the processor 22 may also be stored in memory 24.

The implantable cardiac device 10 preferably also includes pacer circuitry 34 for implementing a dual chamber bradycardia or other pacemaker function. The pacer circuitry 34 operates in a conventional manner to provide pacing pulses to the electrodes 16 positioned in the heart 18 via the leads 14 to maintain a desired cardiac rate. The pacer circuitry 34 preferable receives atrial and ventricular depolarization detection signals directly from the signal detection circuitry 20. The pacing circuitry 34 employs the atrial and ventricular depolarization detection signals from the signal detection circuitry 20 in a conventional manner to, for example, inhibit atrial or ventricular pacing when timely naturally occurring atrial or ventricular depolarizations are detected and, for example, to provide ventricular pacing which tracks a naturally occurring atrial rate. As discussed above, in many patients it is desirable to pace the ventricles in a manner which tracks a naturally occurring atrial rate which corresponds to the metabolic demand of the patient in which the device 10 is implanted.

The processor 22 also preferably monitors the atrial and ventricular depolarization detection signals and other cardiac activity signals provided by the signal detection circuitry 20, and controls the pacer circuitry 34 in response thereto. For example, as will be discussed in more detail below, the processor 22 may monitor atrial depolarization detection signals provided by the signal detection circuitry 20 to determine the atrial rate. If the atrial rate exceeds the maximum atrial tracking rate for pacing, the processor 22 applies an atrial discrimination algorithm to, for example, an electrogram or other atrial activity signal provided by the signal detection circuitry 20, to identify the type of supraventricular tachycardia/atrial flutter which may be occurring. The processor 22 then controls the pacer circuitry 34 to pace the heart 18 in an optimal manner which corresponds to the type of supraventricular tachycardia/atrial flutter identified.

The implantable cardiac device 10 may also include defibrillator/cardioverter circuitry 36 for applying relatively high-level defibrillating or cardioverting electrical energy to the atria and/or ventricles of the heart 18 via the leads 14 and electrodes 16 positioned in the heart 18. As discussed above, the processor 22 monitors the atrial and ventricular activity signals provided thereto by the signal detector circuitry 20. Conventional algorithms known in the art may be used to determine the occurrence of non-pacing terminable atrial or ventricular fibrillation from such signals. In such a case, the processor 22 may control the defibrillator/cardioverter 36 to provide relatively high-level electrical shocks to the ventricles and/or atria to defibrillate and/or cardiovert the heart 18 in a conventional manner. It should be understood, however, that the present invention is particularly applicable to determining optimal pacing therapies in response to the identification of different types of atrial arrhythmias and, therefore, the present invention is particularly applicable to application in bradycardia pacemaker devices which need not include defibrillator/cardioverter circuitry 36.

To complete the description of the exemplary implantable cardiac device 10 in which the present invention may be employed, it is noted that the device 10 may include a receiver/transmitter 38, including an antenna coil 40. The receiver/transmitter 38 may be implemented in a conventional manner to transmit data from the processor 22 out of the implantable device 10 to a remote programmer device (not shown). For example, cardiac activity data detected by the signal detector circuitry 20 may be transmitted to the external device to be stored and analyzed therein in more detail than is possible in the implanted device 10 itself. The receiver/transmitter 38 may also receive programming instructions from the external programmer device for, for example, reprogramming operating parameters of the implantable cardiac advice 10. Communication between the receiver/transmitter 38 and the external programmer device may be implemented in a conventional manner, e.g., via an RF link. The implantable cardiac device 10 also includes a battery 42, which provides power for the processor 22 and other circuit components of the implantable cardiac device 10.

The circuitry for implementing the signal detector 20, processor 22, pacer 34, defibrillator/cardioverter 36, receiver/transmitter 38 and other functions of the implantable cardiac device 10 may be implemented in a conventional manner using analog or digital circuitry, including one or more microprocessors, or any combination thereof. As will be known to those skilled in the art, functions performed by the signal detector 20, pacer 34, defibrillator/cardioverter 36, and receiver/transmitter 38 may be performed by independent analog and/or digital circuitry, as suggested by the illustration of FIG. 1, or may be implemented in one or more processors 22, or in a combination of independent circuits and one or more processors.

The present invention provides a system and method for identifying and providing optimal pacing therapy for different types of atrial based arrhythmias, such as atrial flutter or supraventricular tachycardia. As discussed above, conventional bradycardia pacemakers are designed to correct slow cardiac rhythms. When supraventricular arrhythmias are detected, current bradycardia pacemakers will detect the, e.g., increased atrial rate, and will change pacing modes if the detected atrial rate exceeds the maximum atrial tracking rate to prevent too rapid ventricular pacing at the pathologically high atrial rate. The present invention, however, provides for more sophisticated and effective treatment in response to the detection of a supraventricular tachycardia in an implantable cardiac device, such as a bradycardia pacemaker. In accordance with the present invention, an atrial discrimination algorithm is provided which includes discrimination criteria for distinguishing between different types of supraventricular tachycardia. Pacing of the heart is controlled in a manner corresponding to the type of supraventricular tachycardia identified, in order to provide an optimal pacing therapy for the supraventricular arrhythmia.

A supraventricular tachycardia is a rapid heart rate due to a natural pacemaker located anywhere above the ventricular level, i.e., in the sinus node, atria, or atrial ventricular junction. Atrial flutter, in particular, is a rapid regular atrial contraction occurring at a very high rate, e.g., between 250 and 350 per minute. As used herein, the term supraventricular tachycardia is understood to refer to a rapid regular supraventricular, e.g., atrial, contraction which occurs at a rate less than the atrial flutter rate. As will be discussed in detail below, the present invention employs an atrial discrimination algorithm which includes discrimination criteria for distinguishing between such relatively lower rate supraventricular tachycardia and relatively higher rate atrial flutter. Alternatively, the atrial discrimination algorithm may be said to include discrimination criteria for distinguishing between relatively fast atrial flutter and other atrial flutter. In a third understanding, the atrial discrimination algorithm may include discrimination criteria for distinguishing between different types of supraventricular tachycardia, e.g., supraventricular tachycardia characterized by a relatively fast rapid regular rate and supraventricular tachycardia characterized by relatively lower rapid regular atrial rate. In general, whatever language is employed, it may be said that an atrial discrimination algorithm is employed in accordance with the present invention to distinguish between pathologically rapid regular atrial (supraventricular) contractions of different types, e.g., characterized by different rate ranges or other rate characteristics or waveform morphologies. Based upon the type of supraventricular tachycardia/atrial flutter identified, an appropriate pacing therapy to alleviate the arrhythmia may be selected, and provided to the heart.

Figure 2:
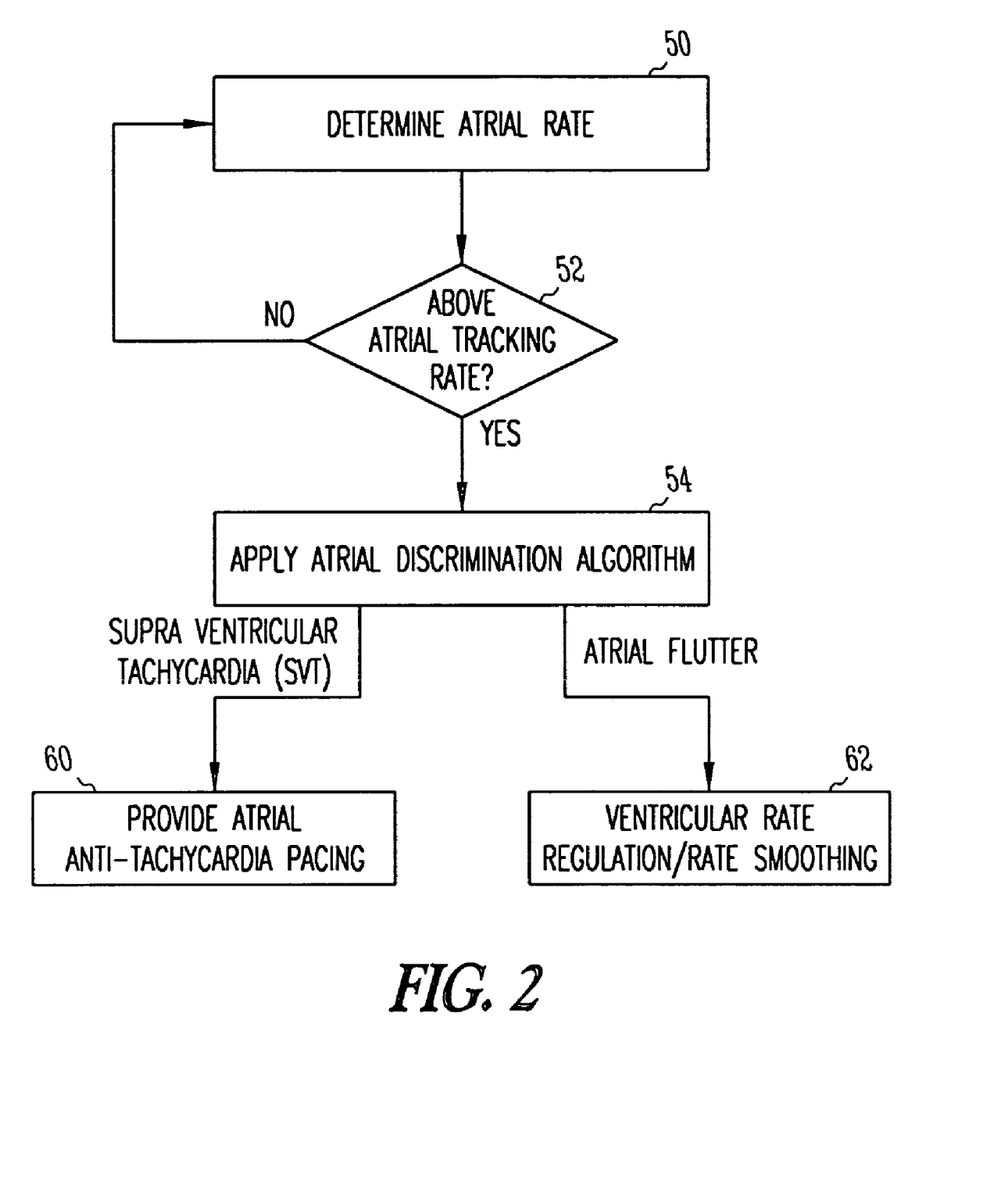
FIG. 2 a flow chart diagram illustrating an exemplary method for determining optimal pacing therapy in response to the identification of different types of atrial arrhythmias in accordance with the present invention.

An exemplary process for using an atrial discrimination algorithm to determine an optimal pacing therapy in accordance with the present invention will now be described in detail with reference to the schematic flow chart diagram of FIG. 2. The exemplary process will be described with reference to the preferred application in a bradycardia pacemaker, or, in general, in an implantable cardiac device configured to provide dual chamber bradycardia pacing. As described above, in dual chamber (DDDR or DDD) bradycardia pacing, ventricular pacing may be provided in a manner which tracks the naturally occurring atrial rate up to a maximum atrial tracking rate. During such pacing, the rate of atrial depolarizations is monitored either continuously or periodically and an atrial rate determined at step 50. The atrial rate may be determined in a conventional manner, e.g., by the processor 22 using atrial depolarization detection indications provided by the signal detector 20 based on atrial activity picked up on one or more electrodes 16 mounted in or near the atria and provided on a lead 14 to the signal detector 20. Conventional rate based counters and averaging techniques may be employed to determine the effective atrial rate.

At step 52 a determination is made whether the atrial rate determined in step 50 is above the maximum atrial tracking rate. As discussed above, the maximum atrial tracking rate is the maximum atrial rate at which ventricular pacing will be allowed to track the atrial rate under normal circumstances. The maximum atrial tracking rate may be established and adjusted by a physician using an external programmer to provide a selected maximum atrial tracking rate to the processor 22 in the implantable cardiac device 10 via the receiver/transmitter 38. If the atrial rate determined in step 50 is not above the atrial tracking rate, the processor 22 continues to monitor the atrial rate until the determined atrial rate does exceed the atrial tracking rate.

If the atrial rate is determined in step 52 to exceed the atrial tracking rate, the processor 22 applies an atrial discrimination algorithm 26 at step 54 to distinguish between different types of supraventricular arrhythmias (supraventricular tachycardia/fast atrial flutter/other atrial flutter) which may be occurring. The atrial discrimination algorithm is preferable applied to an atrial activity signal produced by the signal detector 20 based on cardiac signals detected by one or more electrodes 16 positioned in or near the atria of the heart 18. Depending upon the algorithm employed, different atrial activity signals, e.g., atrial depolarization detection signals or atrial electrogram signals, may be provided by the signal detector 20 to the processor 22 to be analyzed by the atrial discrimination algorithm.

Various different atrial discrimination algorithms for distinguishing between different types of supraventricular tachycardias may be employed. Such atrial discrimination algorithms may include rate-based or other discrimination criteria, for distinguishing between different types of supraventricular tachycardia based on the timing of detected atrial depolarizations. Alternatively, an atrial discrimination algorithm which includes discrimination criteria for distinguishing between different types of supraventricular tachycardia based on the morphology of an atrial electrogram may be employed.

An exemplary highly accurate algorithm which may be implemented in an energy-efficient manner to distinguish between different types of arrhythmias is described in U.S. Pat. No. 6,314,321, filed on Jun. 30, 1999, by Milton M. Morris, and entitled, "Therapy-Selection Methods for Implantable Heart Monitors," which is assigned to the assignee of the present application, and which is incorporated herein by reference. This method employs three statistics, a range statistic, a minimum interval statistic, and a dispersion index, each of which may be calculated from a set of atrial depolarization intervals which indicate the time between successive depolarizations of the atria of a heart. After excluding selected intervals at each extreme, e.g., selected ones of the shortest and longest intervals in the set, the range statistic is calculated as the difference between a first and last one of the remaining intervals, the minimum interval is calculated as the smallest of the remaining intervals, and the dispersion index may be calculated as the standard deviation of the remaining intervals. A scalar quantity, defined as the interval dispersion assessment (IDA), may be calculated as a function of the three statistics. The IDA is compared to one or more threshold values to determine the atrial arrhythmia which is characterized by the particular calculated IDA value. Although the above-referenced patent application describes use of the IDA to distinguish between pacing terminable (e.g., atrial flutter) and non-pacing terminable (e.g., atrial fibrillation) arrhythmias, by selection of the appropriate threshold values this algorithm may also be employed to distinguish between different types of pacing terminable atrial arrhythmias (e.g., between different types of supraventricular tachycardia, fast atrial flutter, or other atrial flutter).

Figure 3:
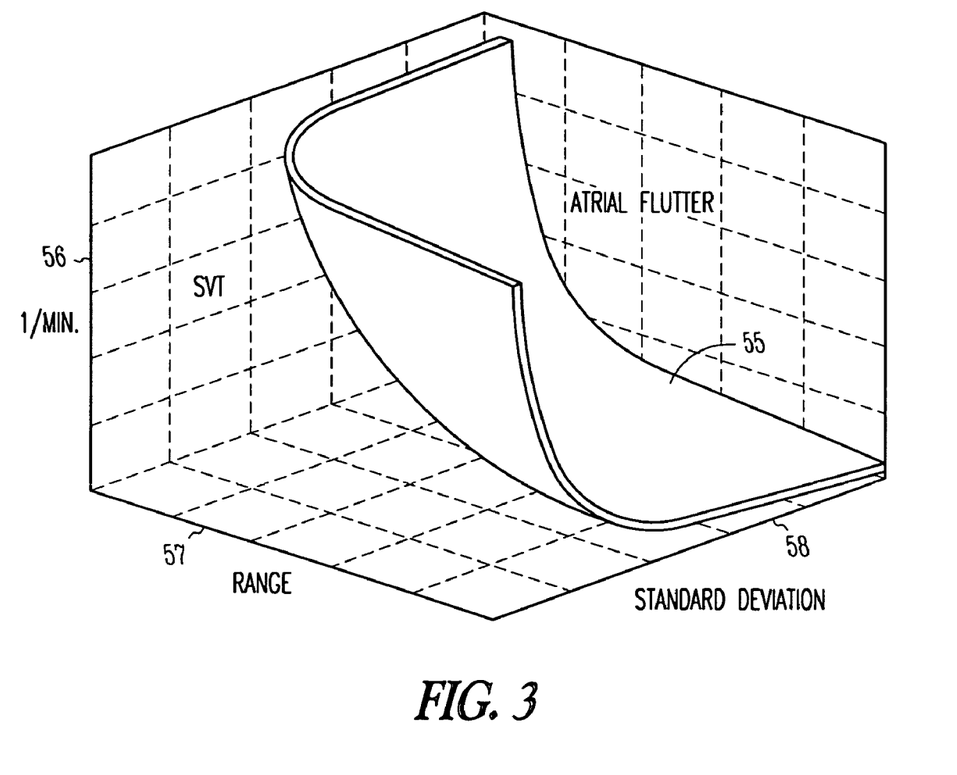
FIG. 3 is a graph of an exemplary three-dimensional atrial discrimination algorithm function which may be employed to distinguish between different types of supraventricular tachycardias for determining an optimal pacing therapy in response thereto in accordance with the present invention.

As described in the above-referenced U.S. Pat. No. 6,314,321, the three atrial depolarization interval based statistics, range, minimum interval, and dispersion index, may be employed to define a threshold function which may be represented as a surface plotted in three-dimensional space. An exemplary threshold function surface 55 plotted in three-dimensional space, defined by an inverse minimum interval axis 56, a range axis 57, and a dispersion (or standard deviation) axis 58, is shown in FIG. 3. The surface 55 represents a set of combinations of minimum interval, range, and dispersion index values such that a combination of such values which plot to a point on one side of the surface 55 indicate the occurrence of a first type of supraventricular tachycardia, e.g., atrial flutter, while a combination of such values which plot to a point on the other side of the surface 55 indicate the occurrence of another type of supraventricular tachycardia, e.g., a slower atrial flutter. The threshold function surface 55 may be derived empirically, e.g., from a sample population, and programmed into the processor 22 of an implanted device 10, to be used as, or as part of, an atrial discrimination algorithm 26. The threshold function surface 55 may be derived from a patient in which an implantable device 10 incorporating a system and method in accordance with the present invention is employed. For example, a physician or the implanted device processor 22 itself, may monitor which types of pacing therapies are effective in a patient in response to detected supraventricular tachycardias of different types, i.e., having different range, minimum interval, and dispersion index statistics, which may be induced in a patient. (A physician may monitor pacing therapy effectiveness in this manner from external to the patient, e.g., using a conventional ECG, or may employ the implanted device 10 itself to induce supraventricular tachycardias, provide pacing therapy, and monitor therapy effectiveness. The physician may then retrieve effectiveness information stored in the device 10 from the device 10, e.g., using an external programmer device via the receiver/transmitter 38.) The position and shape of the threshold function surface 55 employed for atrial discrimination for the patient may be derived from such effectiveness information, or from such information derived from many patients, and programmed into the implanted device processor 22 (e.g., using an external device via the receiver/transmitter 38). Alternatively, or additionally, the device processor 22 itself may be programmed to record the effectiveness of different pacing therapies for treating supraventricular tachycardias of different types occurring in a patient (e.g., having different range, minimum interval, and dispersion index statistics), and to use such information automatically to generate or adjust the threshold surface function 55 employed in a particular patient's implanted device 10.

The result of the step 54 of applying the atrial discrimination algorithm to an atrial activity signal is an indication of the type of supraventricular tachycardia which is occurring. Note that the indication may be entirely internal to the operation of the processor 22. In other words, the indication may simply result from applying the atrial discrimination algorithm to the atrial activity signal, and may or may not be provided outside of the processor 22. The processor 22 responds to the indication by controlling the pacing of the heart in an optimal manner corresponding to the type of supraventricular tachycardia identified.

In response to the indication of the type of supraventricular tachycardia identified by the atrial discrimination algorithm, the processor 22 may control the pacer 34 to provide an appropriate optimal corresponding pacing therapy. For example, if the atrial discrimination algorithm indicates that a supraventricular tachycardia is occurring, i.e., a rapid regular atrial contraction at a relatively low rate (other atrial flutter), the processor 22 may control the pacer 34 to provide atrial anti-tachycardia pacing 60. Such atrial anti-tachycardia pacing may include a rapid series of atrial pacing pulses delivered to the atria via a pacing lead 14 and one or more electrodes 16 positioned in or near the atria of the heart 18. The pacing rate is preferably based on the detected supraventricular tachycardia rate. For instance, the pacer may be programmed to deliver a train of stimuli to the atria at a selected percentage of the cycle length of the supraventricular tachycardia. Either burst or ramp pacing can be used. With burst pacing, the pacing rate or cycle length in the train is constant. With ramp pacing, each successive paced beat has a shortened interval. The details of controlling a pacer 34 to provide atrial anti-tachycardia pacing will be known to those skilled in the art.

If the atrial discrimination algorithm indicates that a more rapid supraventricular tachycardia is occurring, e.g., a fast atrial flutter, the processor 22 may control the pacer 34 to provide a pacing therapy other than atrial anti-tachycardia pacing 62. Such other pacing control may include, for example, ventricular pacing therapy, such as accurate implementation of ventricular rate regulation or Rate Smoothing.

An atrial (supraventricular) arrhythmia may induce a ventricular arrhythmia. Ventricular rate regulation (VRR) controls pacing of the ventricles to regularize the ventricular rate and lengthen short ventricular contraction intervals. It has been found that pacing the ventricles at a rate slightly above the mean ventricular rate can suppress spontaneous ventricular activity. This may be achieved by pacing the ventricles such that, following each sensed beat, the ventricular pacing interval is decreased, and following each paced beat, the pacing interval is increased. An exemplary VRR pacing control method, is described in U.S. patent application Ser. No. 09/316,515, filed May 21, 1999, entitled Method and Apparatus for Treating Irregular Ventricular Contractions Such as During Atrial Arrhythmia, by David B. Krig, et al., which application is assigned to the assignee of the present application. In this application, a VRR pacing interval is calculated based upon a most recent detected V-V interval and the previous VRR pacing interval. For V-V intervals terminating in an intrinsic event, the VRR pacing interval is decreased by an amount related to the previous VRR interval. For V-V intervals terminating in a paced event, the VRR pacing interval is increased by an amount related to the previous VRR pacing interval. The VRR pacing interval is employed as the minimum pacing interval when, e.g., an atrial arrhythmia is detected. Thus, in response to an increasing or irregular ventricular rate, the ventricular pacing rate will increase (shorter pacing interval more likely to result in pacing), whereas the pacing rate will slow to a steady intrinsic rate in response to slowing/stabilization of intrinsic ventricular activity. VRR thus operates to increase the rate of ventricular contractions carefully, to avoid pacing the heart at an unnecessarily high rate. VRR methods other than those described herein may also be employed in accordance with the present invention, e.g., in response to the determination by an atrial discrimination algorithm that a relatively rapid rate supraventricular tachycardia (e.g., atrial flutter) is occurring.

Rate Smoothing is a variation of upper rate behavior in a pacemaker which was introduced by Cardiac Pacemakers, Inc. of St. Paul, Minn., as a method of preventing marked changes in cycle length not only at the upper rate limit of a dual chamber pacemaker but also at any time that the sinus rate is accelerating or decelerating. With Rate Smoothing, the pacer 34 is programmed to a percentage change that will be allowed between VV cycles, that is, e.g., 3, 6, 9, or 12 percent. For example, if the VV cycle length is stable at 900 milliseconds during atrial tracking pacing, Rate Smoothing is "on" at 6 percent, and the atrial rate suddenly accelerates, the subsequent VV cycle cannot accelerate by more than 54 milliseconds, which is 6 percent of 900 milliseconds. The ventricular rate is therefore relatively smooth.

It should be understood that a pacer 34 may be controlled to provide other pacing therapies to the heart in response to the identification of different types of supraventricular tachycardia occurring therein. It is envisioned that, as technology evolves, different and more appropriate pacing therapies for different types of supraventricular tachycardias may be developed. Such pacing therapies may be incorporated into the method and apparatus of the present invention which provides for distinguishing between different types of supraventricular tachycardias in order to select an optimal pacing therapy to be provided to the heart in response thereto.

In accordance with the present invention, an atrial discrimination algorithm may be employed both to determine an optimal pacing therapy to be provided in response to a detected supraventricular tachycardia, as well as to optimize the timing of such therapy. This may be achieved, for example, by tracking and/or trending the output of the atrial discrimination algorithm to determine when a supraventricular arrhythmia is likely to occur, and thus to optimize when pacing therapy should be initiated. For example, the atrial discrimination algorithm may be applied continuously, e.g., every cardiac cycle, or every several cardiac cycles, as computation resources in the processor 22 allow, to an atrial activity signal. As discussed above, the output of the atrial discrimination algorithm may be a value, e.g., the IDA or three coordinate values corresponding to a point in the three-dimensional space of FIG. 3, which indicates a type of supraventricular tachycardia, if any, which may be occurring. This atrial discrimination algorithm output value may be saved for tracking of the value over an extended period of time by the processor 22. The trend in the atrial discrimination algorithm output values may indicate, for example, that atrial activity is trending toward, for example, a particular type of supraventricular tachycardia, for which a particular optimal pacing therapy is indicated. Thus, the processor 22 may be programmed to analyze the trend in atrial discriminating algorithm output values to thereby prepare the pacer circuitry 34 to respond with the appropriate pacing therapy at the optimal time.

It should be noted that the present invention may be incorporated as part of an implantable cardiac device which provides both dual chamber bradycardia pacing and atrial defibrillation. In such a device, an atrial activity signal may be monitored to determine if atrial fibrillation is occurring. If atrial fibrillation is detected, the processor 22 may control the defibrillator/cardioverter 36 to provide a relatively high-energy electrical shock (at an energy level higher than the pacing pulses) to the atria, preferably in synchronism with a detected or paced ventricular depolarization, to cardiovert the atria. Such atrial fibrillation detection and cardioversion may be accomplished simultaneously with and as an integrated part of the process described above for distinguishing between different types of rapid regular supraventricular tachycardias and providing a selected optimal pacing therapy in response thereto, in accordance with the present invention.

By providing a method and apparatus for distinguishing between different types of regular supraventricular tachycardias occurring in a patient's heart, the present invention also allows for comprehensive diagnostics for atrial arrhythmias for such patients, allowing for capture of AF burden data. For example, the types of supraventricular tachycardias identified in a patient may be stored in memory 24 and transmitted, via receiver/transmitter 38, to an external device for further analysis by the patient's physician.

It is understood that the present invention is not limited to the particular exemplary applications and embodiments illustrated and described herein, but embraces such modified forms thereof which come within the scope of the following claims.

What is claimed is:

1. A method for distinguishing between different types of rapid regular supraventricular tachycardia, comprising:
   establishing an atrial discrimination algorithm including discrimination criteria for distinguishing between different types of rapid regular supraventricular tachycardia;
   sensing activity of at least one of the atria of the heart to provide an atrial activity signal;
   applying the atrial discrimination algorithm to the atrial activity signal to compare at least one characteristic of said atrial activity signal to the discrimination criteria to identify the type of rapid regular supraventricular tachycardia occurring; and
   providing an indication corresponding to the type of rapid regular supraventricular tachycardia identified,
   wherein establishing an atrial discrimination algorithm includes establishing discrimination criteria for distinguishing between fast atrial flutter at a first high rate and an other atrial flutter at a second lower rate.

2. The method of claim 1 wherein establishing an atrial discrimination algorithm includes establishing discrimination criteria for distinguishing between fast atrial flutter and a slower rate rapid regular supraventricular tachycardia.

3. The method of claim 1 wherein establishing an atrial discrimination algorithm includes establishing rate-based discrimination criteria for distinguishing between different types of rapid regular supraventricular tachycardia and wherein comparing at least one characteristic of the atrial activity signal to the discrimination criteria includes comparing a rate of the atrial activity signal to the discrimination criteria.

4. The method of claim 1 wherein establishing an atrial discrimination algorithm includes establishing morphology-based discrimination criteria for distinguishing between different types of rapid regular supraventricular tachycardia and wherein comparing at least one characteristic of the atrial activity signal to the discrimination criteria includes comparing a morphology characteristic of the atrial activity signal to the discrimination criteria.

5. The method of claim 1 wherein establishing an atrial discrimination algorithm includes establishing a multi-dimensional threshold function, and wherein applying the atrial discrimination algorithm to the atrial activity signal includes comparing a combination of a plurality of statistics calculated from a set of depolarization intervals determined from the atrial activity signal to the threshold function.

6. The method of claim 1 comprising establishing a maximum atrial tracking rate, deriving an atrial rate from an atrial activity signal, and comparing the derived atrial rate to the maximum atrial tracking rate, and wherein applying the atrial discrimination algorithm to an atrial activity signal includes applying the atrial discrimination algorithm only if the derived atrial rate exceeds the maximum atrial tracking rate.

7. The method of claim 1 comprising controlling pacing of a heart in a manner corresponding to the type supraventricular tachycardia identified.

8. An implantable cardiac device, comprising:
sensing means for sensing activity of at least one of the atria of a heart;
signal detection means coupled to the sensing means for generating an atrial activity signal based on the sensed activity of the atria of the heart; and
a processor coupled to the signal detection means for receiving the atrial activity signal and for applying an atrial discrimination algorithm including discrimination criteria for distinguishing between different types of rapid regular supraventricular tachycardia to the atrial activity signal to compare at least one characteristic of the atrial activity signal to the discrimination criteria to identify the type of rapid regular supraventricular tachycardia occurring and for providing an indication corresponding to the type of rapid regular supraventricular tachycardia identified,
wherein the atrial discrimination algorithm includes discrimination criteria for distinguishing between fast atrial flutter and a slower rate rapid regular supraventricular tachycardia, and
wherein the atrial discrimination algorithm includes discrimination criteria for distinguishing between fast atrial flutter at a first high rate and another atrial flutter at a second lower rate.

9. The implantable cardiac device of claim 8 wherein the sensing means includes at least one electrode positioned in the heart and wherein the signal detection means is coupled to the electrode by a lead.

10. The implantable cardiac device of claim 8 wherein the atrial discrimination algorithm includes rate-based discrimination criteria for distinguishing between different types of rapid regular supraventricular tachycardia and wherein the processor compares a rate characteristic of the atrial activity signal to the discrimination criteria to identify the type of rapid regular supraventricular tachycardia occurring.

11. The implantable cardiac device of claim 8 wherein the atrial discrimination algorithm includes morphology-based discrimination criteria for distinguishing between different types of rapid regular supraventricular tachycardia and wherein the processor compares a morphology characteristic of the atrial activity signal to the discrimination criteria to identify the type of rapid regular supraventricular tachycardia occurring.

12. The implantable cardiac device of claim 8 wherein the atrial discrimination algorithm includes a multi-dimensional threshold function and wherein the processor compares a combination of a plurality of statistics calculated from a set of depolarization intervals determined from the atrial activity signal to the threshold function to identify the type of rapid regular supraventricular tachycardia occurring.

13. The implantable cardiac device of claim 8 comprising additionally a pacer for providing pacing pulses to the heart and wherein the processor is coupled to the pacer for controlling the pacer to provide pacing of the heart in a manner corresponding to the type of supraventricular tachycardia identified.

14. The implantable cardiac device of claim 13 wherein the pacer is dual chamber bradycardia pacer for providing pacing pulses to ventricles of the heart at a pacing rate based on a detected atrial rate up to a maximum atrial tracking rate and wherein the processor applies the atrial detection algorithm to the atrial activity signal only if the detected atrial rate exceeds the maximum atrial tracking rate.

15. An implantable cardiac device, comprising:
sensing means for sensing activity of at least one atria of a heart;
signal detection means coupled to the sensing means for generating an atrial activity signal based on the sensed activity of the at least one atria of the heart;
a processor coupled to the signal detection means for receiving the atrial activity signal and for applying an atrial discrimination algorithm to the atrial activity signal to compare at least one characteristic of the atrial activity signal to discrimination criteria, wherein the atrial discrimination algorithm is adapted to discriminate between a fast atrial flutter at a first high rate and another atrial flutter at a second lower rate, and wherein the processor is adapted to provide an indication corresponding to the fast atrial flutter at a first high rate and the other atrial flutter at a second lower rate.

16. A method for providing therapy to a heart, comprising:
establishing discrimination criteria for distinguishing at least two different types of supraventricular tachycardia having regular rapid supraventricular heart rates;
sensing activity of at least one atria of the heart to provide an atrial activity signal;
determining that an atrial rate is above a predetermined atrial tracking rate for performing ventricular pacing such that the atrial rate is higher than the ventricular rate;
in response to determining that the atrial rate is above the predetermined atrial tracking rate, providing an atrial discrimination therapy output based on the atrial activity signal, including comparing at least one characteristic of the atrial activity signal to the discrimination criteria to identify one of the at least two different types of supraventricular tachycardia having regular rapid supraventricular heart rates; and
providing an atrial anti-tachycardia pacing therapy to the heart for an identified first one of the at least two different types of supraventricular tachycardia and providing a ventricular pacing therapy for an identified second one of the at least two different types of supraventricular tachycardia, wherein establishing an atrial discrimination algorithm includes establishing discrimination criteria for distinguishing between fast atrial flutter at a first high rate and an other atrial flutter at a second lower rate.

17. The method of claim 16 further comprising:
trending the atrial discrimination therapy output; and
timing a pacing therapy based on the trended atrial discrimination therapy output.

18. A method for providing pacing therapy to a heart, comprising:
establishing discrimination criteria for distinguishing at least two different types of supraventricular tachycardia having regular rapid supraventricular heart rates;
sensing activity of at least one atria of the heart to provide an atrial activity signal;
comparing at least one characteristic of the atrial activity signal to the discrimination criteria to identify one of the at least two different types of supraventricular tachycardia having regular rapid supraventricular heart rates; and
providing an indication corresponding to the type of regular rapid supraventricular tachycardia identified,
wherein establishing an atrial discrimination algorithm includes establishing discrimination criteria for distinguishing between fast atrial flutter at a first high rate and an other atrial flutter at a second lower rate.

19. The method of claim 18 wherein providing an indication corresponding to the type of regular rapid supraventricular tachycardia identified includes controlling pacing of the heart in a first manner for an identified first one of the at least two different types of supraventricular tachycardia and in a second manner for an identified second one of the at least two different types of supraventricular tachycardia.

20. The method of claim 19 wherein controlling pacing of the heart in a first manner for an identified first one of the at least two different types of supraventricular tachycardia and in a second manner for an identified second one of the at least two different types of supraventricular tachycardia includes controlling pacing of the heart to provide atrial antitachycardia pacing to the heart if a slower rate supraventricular tachycardia is identified as occurring and providing a second type of pacing control if a fast atrial flutter is identified as occurring.

21. The method of claim 19 wherein controlling pacing of the heart in a first manner for an identified first one of the at least two different types of supraventricular tachycardia and in a second manner for an identified second one of the at least two different types of supraventricular tachycardia includes providing an atrial anti-tachycardia pacing therapy to the heart for an identified first one of the at least two different types of supraventricular tachycardia and providing a ventricular pacing therapy for an identified second one of the at least two different types of supraventricular tachycardia.

22. The method of claim 18 wherein establishing discrimination criteria includes establishing an atrial discrimination algorithm, the algorithm providing discrimination criteria for distinguishing different types of regular rapid supraventricular tachycardia.

23. An implantable cardiac device, comprising:
means for sensing activity of at least one atria of the heart to provide an atrial activity signal;
means for comparing at least one characteristic of the atrial activity signal to discrimination criteria to identify one of at least two different types of supraventricular tachycardia having regular rapid supraventricular heart rates; and
means for providing an indication corresponding to the type of regular rapid supraventricular tachycardia identified,
wherein the means for comparing includes:
signal detection means coupled to the means for sensing to generate an atrial activity signal based on the sensed activity of the at least one atria of the heart; and
a processor coupled to the signal detection means for receiving the atrial activity signal and for applying an atrial discrimination algorithm including discrimination criteria for distinguishing different types of rapid regular supraventricular tachycardia to the atrial activity signal to compare at least one characteristic of the atrial activity signal to the discrimination criteria to identify a type of rapid regular supraventricular tachycardia occurring, the processor including the means for providing an indication corresponding to the type of rapid regular supraventricular tachycardia identified,
wherein the atrial discrimination algorithm is adapted to discriminate between a fast atrial flutter at a first high rate and an other atrial flutter at a second lower rate, and wherein the processor is adapted to provide an indication corresponding to an identified one of the fast atrial flutter at a first high rate and the other atrial flutter at a second lower rate.

24. The device of claim 23 further comprising means for providing pacing pulses to a heart, wherein the means for providing an indication controls the means for providing pacing pulses to a heart.

25. The device of claim 23 wherein the means for providing pacing pulses to a heart includes a dual chamber bradycardia pacer for providing pacing pulses to ventricles of the heart at a pacing rate based on a detected atrial rate up to a maximum atrial tracking rate; and the means for providing an indication applies an atrial detection algorithm only if the detected atrial rate exceeds the maximum atrial tracking rate.

26. A method for providing pacing therapy to a heart, comprising:
sensing activity of at least one atria of the heart to provide an atrial activity signal;
analyzing the atrial activity signal to discriminate between at least two different types of supraventricular tachycardia having regular rapid supraventricular heart rates;
providing a first pacing therapy for an identified first one of the at least two different types of supraventricular tachycardia and a second pacing therapy for an identified second one of the at least two different types of supraventricular tachycardia; and
trending the atrial activity signal to appropriately time at least one of the first and second pacing therapies,
wherein:
the first one of the at least two different types of supraventricular tachycardia includes a first atrial flutter at a first rate;
the second one of the at least two different types of supraventricular tachycardia includes a second atrial flutter at a second rate, the second rate being slower than the first rate;
the first pacing therapy includes ventricular pacing; and
the second pacing therapy includes atrial anti-tachycardia pacing.

* * * * *